United States Patent
Pernel

(10) Patent No.: US 7,690,244 B2
(45) Date of Patent: Apr. 6, 2010

(54) METHOD FOR MEASURING FOR PERMEABILITY TO GASES WITH RAPID CONDITIONING AND INSTALLATION FOR CARRYING OUT THIS METHOD

(75) Inventor: Yann Pernel, Octeville sur Mer (FR)

(73) Assignee: Sidel Participations, Octeville sur Mer (FR)

( * ) Notice: Subject to any disclaimer, the term of this patent is extended or adjusted under 35 U.S.C. 154(b) by 146 days.

(21) Appl. No.: 11/913,985

(22) PCT Filed: May 10, 2006

(86) PCT No.: PCT/FR2006/001045
§ 371 (c)(1),
(2), (4) Date: Nov. 9, 2007

(87) PCT Pub. No.: WO2006/120345
PCT Pub. Date: Nov. 16, 2006

(65) Prior Publication Data
US 2008/0184777 A1  Aug. 7, 2008

(30) Foreign Application Priority Data
May 10, 2005 (FR) .................................. 05 04689

(51) Int. Cl.
*G01N 15/08* (2006.01)
(52) U.S. Cl. .............................. 73/38; 73/1.02; 73/1.06
(58) Field of Classification Search .................... 73/38, 73/1.02, 1.06
See application file for complete search history.

(56) References Cited

U.S. PATENT DOCUMENTS

| 5,081,863 | A | 1/1992 | Reid |
| 6,450,012 | B1 | 9/2002 | Mayer et al. |
| 6,561,008 | B1 | 5/2003 | Mulholland et al. |
| 6,857,307 | B2 * | 2/2005 | Gebele et al. ................. 73/38 |
| 2002/0014154 | A1 * | 2/2002 | Witzko et al. ................ 95/178 |
| 2002/0162384 | A1 | 11/2002 | Sharp et al. |
| 2004/0040372 | A1 | 3/2004 | Plester et al. |

FOREIGN PATENT DOCUMENTS

FR  2 844 596 A  3/2003

* cited by examiner

*Primary Examiner*—Hezron Williams
*Assistant Examiner*—Rodney T Frank
(74) *Attorney, Agent, or Firm*—Sughrue Mion, PLLC

(57) ABSTRACT

The invention relates to a method for measuring the permeability to gases of the wall of a hollow body (6) made of polymeric material, characterized: in that it comprises a first conditioning step during which a flushing gas flushes said hollow body (6), and a second measuring step during which a measurement gas is introduced into said hollow body (6); in that the flow of flushing gas is greater than the flow of the measurement gas, and; the flushing gas is sent into the hollow body (6) without mixing with the measurement gas.

10 Claims, 2 Drawing Sheets

METHOD FOR MEASURING FOR PERMEABILITY TO GASES WITH RAPID CONDITIONING AND INSTALLATION FOR CARRYING OUT THIS METHOD

TECHNICAL FIELD

The present invention relates to the technical field of the measurement of the permeability to gases of polymer walls such as, in particular, but not exclusively, walls of hollow bodies such as bottles, for example made from polyethylene terephthalate (PET).

BACKGROUND ART

As opposed to glasses, metals and metal alloys, and to ceramics, polymer materials are relatively permeable to gases and to moisture. The transfer of oxygen across the walls of a receptacle containing a beverage may ultimately cause the oxidation of certain compounds such as vitamins, fatty acids and proteins. Similarly, a loss of flavor and, more generally, a loss of organoleptic properties may result from weak barrier properties of a food container.

Under the very general term of permeability, three mechanisms can be distinguished:
  sorption and desorption on the inside walls of the receptacles;
  diffusion across the walls of the receptacles;
  migration of certain compounds from the polymer material forming the receptacle to the content of this receptacle.

Techniques for measuring the permeability of polymer materials are usually concerned with sheet materials and can be classed in three categories: measurements at variable pressure, measurements at variable volume, measurements called isostatic and isobaric measurements.

Various instruments for measuring the permeability, whether to oxygen or to carbon dioxide, are available on the market. Thus, in particular, instruments are sold, under the trade name Ox-tran®, for measuring the permeability to oxygen, and are sold under the trade name Permatran® for measuring the permeability to carbon dioxide (cf. for example document U.S. Pat. No. 6,699,320 (column 4, lines 7 to 16)).

In order to investigate the permeation properties of a three-dimensional container made from a flexible material—like PET, for example—in its geometry of use, this container is merely placed in a test gas atmosphere and a stream of carrier gas is circulated inside the container, the outgoing stream being conveyed to a detection and measuring instrument.

However, due in particular to the sorption of oxygen, and to avoid artefacts, it is necessary first to purge the hollow bodies such as bottles, before actually taking the permeability measurement. This first step is called conditioning.

After this conditioning is completed, a steady state is obtained, in which the permeation measurements can be taken.

To reduce the conditioning time, it has been proposed to place the polymer container under vacuum beforehand (see US 2004/0177676), this technique incurring major risks of irremediable deterioration of the container during the measurement.

Conventionally, after conditioning, to measure the permeability to oxygen, air or oxygen is introduced in a continuous stream of a mixture comprising a high proportion of nitrogen and a low proportion of hydrogen (between 0.5% and 5% hydrogen, typically two percent hydrogen in known instruments for measuring permeability to oxygen). This continuous stream is sent at a very low flow rate, about 10 milliliters per minute. The oxygen is removed by the nitrogen, the carrier gas, and the quantity of oxygen is measured by coulometry.

If the polymer material tested has weak barrier properties, air is employed for the measurement.

For materials basically having good or even very good barrier properties, such as in particular PET receptacles coated with amorphous carbon by the use of plasma deposition technologies, such as the technology described in document EP 1 068 032 which has been developed by the applicant, oxygen is employed for the measurement.

For measuring permeability to carbon dioxide, with known measuring instruments, three methods are provided:
  a first method called accumulation, for materials having permeability values lower than 55 cc per square meter and per day. In this first method, an infrared sensor compares the signal obtained for a reference quantity of carbon dioxide in a reference cell and the quantity of carbon dioxide which has passed through the polymer material and has accumulated in a measurement cell, having the same volume as the reference cell;
  a second method called the dynamic method, employed for polymer materials having permeability values above 50 cc per square meter and per day. In this second method, when the carbon dioxide passes through the polymer material to be tested to pass into a measurement cell, a current value is obtained by the infrared sensor. As this current value changes linearly with time, a steady state condition is obtained and the steady state signal obtained is compared with the signal obtained when a predefined quantity of $CO_2$ is injected into a volume identical to that of the measurement cell;
  a third method called the continuous flow method. In this third method, employed for polymer materials having a permeability of between 30 and 10 000 cc per square meter and per day, and if a large number of samples need to be tested, the carbon dioxide passed through the polymer material is mixed with nitrogen, and it is this mixture which passes in front of the infrared sensor. The value obtained is compared to that of a reference.

Conditioning is a lengthy step, designed to ensure that the test conditions are at equilibrium.

This conditioning time depends on many factors, such as the barrier properties of the polymer material, the thickness of the polymer material, and the temperature.

When the measurement is taken on a bottle, the conditioning time is commensurate with the developed surface area of the bottle as stated in document FR 2 844 596.

It is routine practice for a person skilled in the art for the conditioning time to be about fifteen to twenty hours, which raises numerous practical problems for tracking the measurements. It is moreover not possible, with techniques known today to the applicant, to take more than one measurement per cell and per 24 hours.

It is the object of the invention to provide a conditioning method and installation for a measurement that is far more rapid and yet just as accurate and reliable.

SUMMARY OF THE INVENTION

For this purpose, the invention relates, according to a first aspect, to a method for measuring the permeability to gases of the wall of a hollow body made from polymer material, characterized in that it comprises a first step called the conditioning step in which a flushing gas flushes said hollow body, and a second step, called the measuring step, in which a measurement gas is introduced into said hollow body, in that the flow rate of flushing gas is higher than the flow rate of measurement gas and in that said flushing gas is sent into said hollow body without mixing with said measurement gas.

According to one embodiment, with regard to said polymer wall, the flow rate of flushing gas is more than ten times higher than the flow rate of measurement gas.

According to a particular embodiment, the flow rate of flushing gas is, with regard to said wall, about 200 cc per minute, the flow rate of measurement gas, with regard to said wall, being about ten ml per minute.

Advantageously, the flushing gas and the measurement gas are different. Thus, for the measurement or the permeability to oxygen, the flushing gas can be an inexpensive gas, such as standard industrial nitrogen, the measurement gas for its part being more expensive for example, nitrogen mixed with a proportion of hydrogen of between 0.5% and 5%.

In one embodiment, the method comprises a step for measuring a quantity of gas by coulometry, for example using an Ox-tran® instrument sold by Mocon or a similar instrument.

According to a second aspect, the invention relates to an installation for implementing the method for measuring the permeability of the wall of a hollow body made from polymer material, characterized in that it comprises a first circuit of a flushing gas suitable for flushing the hollow body and a second circuit of a measurement gas introduced into said hollow body, these two circuits being partly common and connected to one another via fluid distribution means so that the measurement gas is sent into said hollow body without mixing with said measurement gas.

In one embodiment, the distribution means comprise at least two inlets and one outlet and each inlet can be communicated selectively with the outlet.

In one embodiment, the distribution means consist of a valve comprising at least two ports which may be opened separately, said ports each having one inlet and one outlet; preferably, the two ports are connected at their outlet, so that the outlet can be supplied by one or the other of the ports.

In a particular embodiment, a first inlet of the distribution means is connected to a measurement gas distribution source associated with an instrument for measuring the quantity of a given gas, for example oxygen or carbon dioxide, a second inlet of the distribution means is connected to a source of flushing gas, and the outlet of the valve communicates fluidly with one side of the polymer wall, a line moreover making said polymer wall side communicate fluidly with the instrument for measuring the quantity of gas.

According to a third aspect, the invention relates to the application of the abovementioned method or installation for measuring the permeability of a hollow body to oxygen or to carbon dioxide, such as for example a plug, a box or a bottle, particularly a PET bottle.

By significantly shortening the conditioning time, and without any risk of deterioration of the hollow body, the method and installation of the invention are particularly advantageous for measuring the permeability of receptacles, such as bottles, made from PET, fabricated by blowing (or drawing/blowing) in dies or having undergone a treatment consisting in depositing a barrier coating after their manufacture, in order to improve their impermeability to gases. In fact, both during the phases of adjustment of the settings of the receptacle blowing or treatment machines, and during their industrial operating phases, it is necessary to take impermeability measurements to judge the proper settings of the machines and/or their production quality. These measurements are taken on a sufficient number of receptacles to constitute representative samples, and the invention therefore serves to analyze a sample of a given size more rapidly than a device of the prior art, or, in the same time interval, to analyze a sample of larger size than could be done by a device of the prior art.

BRIEF DESCRIPTION OF THE DRAWINGS

Other objects and advantages of the invention will be apparent from the following description of embodiments, a description provided with reference to the appended drawings, in which.

Figure 1:
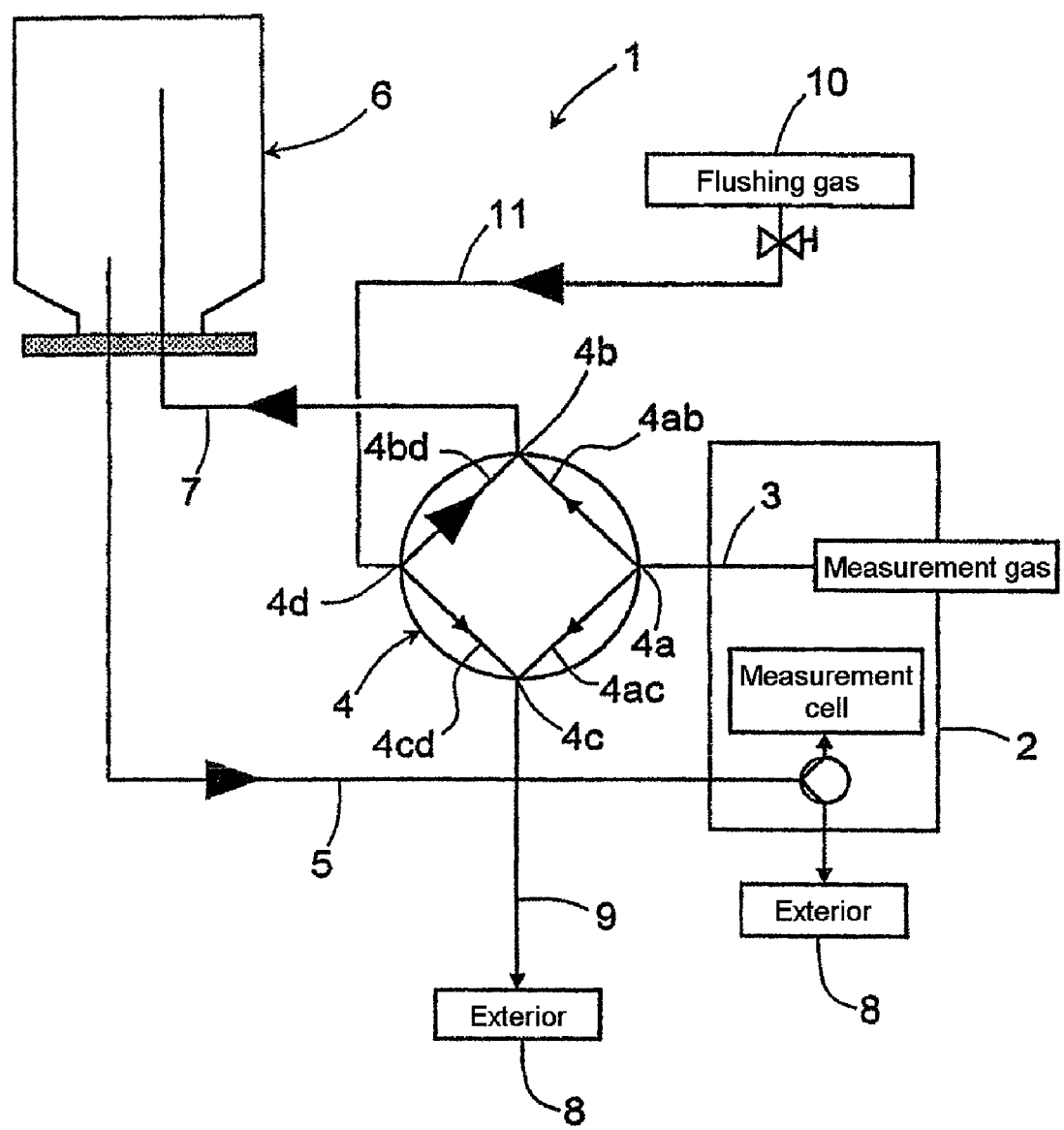
FIG. 1 is a schematic illustration of an installation for measuring the permeability of a hollow body comprising a conditioning device according to one embodiment, in a first operating phase.

DESCRIPTION OF THE PREFERRED
EMBODIMENT OF THE INVENTION

The measurement installation 1 comprises a gas analyzer 2, for example of the type sold under the Mocon reference Ox-tran.

This gas analyzer 2 comprises a portion designed to supply measurement gas and a measurement cell.

The measurement gas outlet is connected, via a first line 3, to a first inlet 4a of fluid distribution means 4 of the four-way type (more precisely having two inlets 4a, 4d, and two outlets 4b, 4c). Thus, the distribution means 4 comprise at least two inlets 4a, 4d and one outlet 4b, and each inlet 4a, 4d can be placed in selective communication with the outlet 4b. The measurement cell is connected, via a second line 5, to the hollow body 6 to be tested.

A third line 7 connects the outlet 4b of the distribution means 4 to the hollow body 6.

A fourth line 9 connects the outlet 4c of the distribution means 4 to the external air 8.

Finally, a fifth line 11 connects the inlet 4d of the distribution means 4 to the flushing gas source 10.

Briefly, a first inlet 4a of the distribution means 4 is connected to a measurement gas distribution source associated with an instrument 2 for measuring the quantity of a given gas. A second inlet 4d of the distribution means 4 is connected to a source 10 of flushing gas, and the outlet 4b of the valve 4 communicates fluidly with one side of the polymer wall, a line 5 moreover making the polymer wall side communicate fluidly with the instrument for measuring the quantity of gas.

In a first step, shown in FIG. 1, an inert flushing gas, for example nitrogen, is sent, via a fifth line 11, from the source 10 to the inlet 4d of the distribution means 4, and is then entrained via a port 4bd of said means 4 to the outlet 4b of the valve 4, to be sent toward the hollow body 6, via the third line 7.

It should be observed that during this flushing step, only the port 4bd of the means 4 is open, the other ports 4ab (which connects the inlet 4a to the outlet 4b), 4ac (which connects the inlet 4a to the outlet 4c) and 4cd (which connects the inlet 4d to the outlet 4c) being closed.

This inert gas flushes the hollow body 6 and exits therefrom via the second line 5, to pass through the analyzer 2, and to be discharged to the external surrounding air.

This inert gas is advantageously sent at a high flow rate, into this first circuit, for example about 200 cc per minute.

Figure 2:
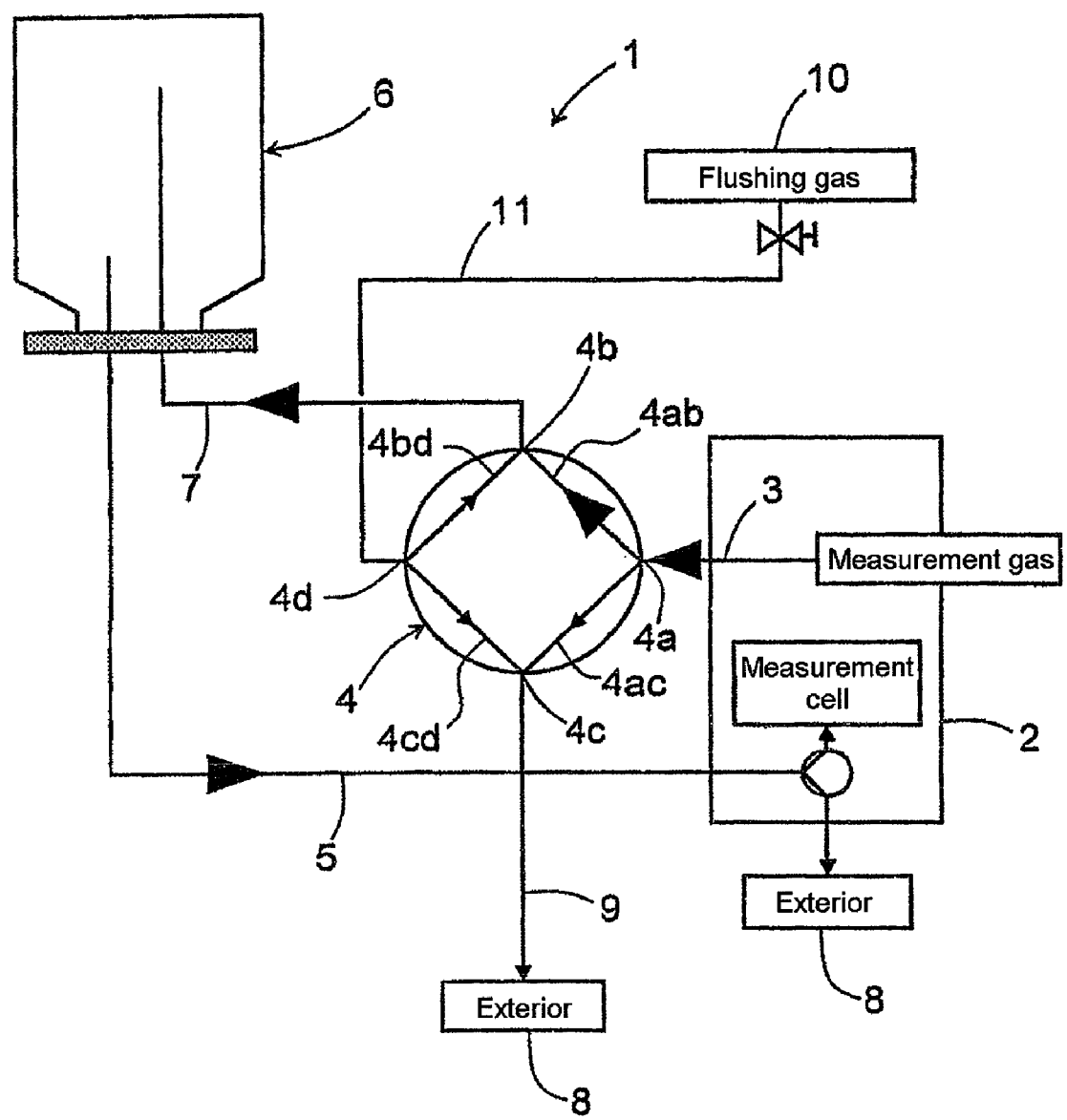
FIG. 2 is a schematic illustration of the installation of FIG. 1, in a second operating phase.

In a second step, shown in FIG. 2, the measurement gas is sent to the first inlet 4a of the means 4, via the first line 3, and this gas passes, via the port 4ab, from the first inlet 4a to the outlet 4b to be introduced into the hollow body 6, via the third line 7.

The measurement gas is sent at a low flow rate, of about 10 ml per minute, and it leaves the hollow body 6 via the second line 5 to go toward the measurement cell of the analyzer 2.

It should be observed that during this measurement step, only the port 4ab of the distribution means 4 is open, the other ports 4bd (which connects the inlet 4d to the outlet 4b), 4ac (which connects the inlet 4a to the outlet 4c) and 4cd (which connects the inlet 4d to the outlet 4c) being closed.

By the arrangements described above, the gas circuit used for conditioning (first step shown in FIG. 1) is partly distinct from the gas circuit used for the permeability measurement (second step shown in FIG. 2), contrary to conventional permeameters.

The hollow body 6 to be tested can thereby be flushed, before the measurement, by a first gas such as nitrogen, less costly than the measurement gas, and this first gas can be sent at a high flow rate into the hollow body, without the risk of mixing with the measurement gas.

In other words, the method according to the invention for measuring the permeability to gases of the wall of a hollow body 6 made from a polymer material comprises a first step called the conditioning step, in which a flushing gas flushes the hollow body 6, and a second step, called the measurement step, in which a measurement gas is introduced into said hollow body 6, the flow rate of flushing gas being higher than the flow rate of measurement gas and the flushing gas being sent into the hollow body 6 without mixing with the measurement gas, the flow rate of flushing gas being more than ten times higher than the flow rate of measurement gas.

Preferably, the flushing gas and the measurement gas are different, and even more preferably for measuring the permeability to oxygen, the flushing gas is nitrogen, the measurement gas then being nitrogen mixed with a proportion of hydrogen of between 0.5 and 5%.

Additionally, the method of the invention comprises a step for measuring a quantity of gas by coulometry.

Obviously, the hollow body to be tested is fixed tightly to a measurement support, in a manner known per se.

The time required for proper conditioning can be controlled using conventional comparative tests. The applicant has thereby succeeded in reducing a conditioning time of 16 hours to a time of half an hour, for measuring the permeability of a 26.5 g PET bottle.

As previously observed, during the flushing or measurement steps, the ports 4ac and 4cd of the distribution means 4 are closed. In fact, these ports are not indispensable, but are preferable in order to facilitate the purging of the circuits: for this purpose, the outlet 4c of the distribution means 4 is connected to the external air, and the ports 4ac and 4cd are then opened in the event of a purge.

It therefore appears that the outlet 4c and the ports 4ac and 4cd are not indispensable, but preferable.

It should be observed that the installation and the method of the invention do not modify the structure and the operation of the gas analyzers, such as the Mocon Ox-tran for example.

Briefly, the invention also relates to an installation for implementing the method for measuring the permeability of the wall of a hollow body 6 made from a polymer material, characterized in that it comprises a first circuit of a flushing gas suitable for flushing the hollow body 6 and a second circuit of a measurement gas introduced into the hollow body 6, these two circuits being partly common and connected one to the other via fluid distribution means 4 so that the measurement gas is sent into the hollow body 6 without mixing with the measurement gas.

The method, as previously described, and the installation, as previously described, apply more particularly to the measurement of the permeability of a hollow body 6 to oxygen or to carbon dioxide.

It is understood that the method and installation of the invention are particularly advantageous for measuring permeabilities to gases of hollow bodies such as bottles, but the invention can be implemented for measuring permeabilities of films to gases.

The invention claimed is:

1. A method for measuring a permeability to gases of a wall of a hollow body made from a polymer material, the method comprising:
    a first step, called a conditioning step, in which a flushing gas flushes said hollow body;
    a second step, called a measuring step, in which a measurement gas is introduced into said hollow body; and
    a third step in which the measurement gas is measured, after the measurement gas is introduced into said hollow body, to measure the permeability of the hollow body;
    wherein a flow rate of the flushing gas is higher than a flow rate of the measurement gas; and
    wherein said flushing gas is sent into said hollow body without mixing with said measurement gas.

2. The measurement method as claimed in claim 1, wherein the flow rate of the flushing gas is more than ten times higher than the flow rate of the measurement gas.

3. The measurement method as claimed in claim 1, wherein the flow rate of flushing gas is about 200 cc per minute and wherein the flow rate of measurement gas is about ten cc per minute.

4. The measurement method as claimed in claim 1, wherein the flushing gas and the measurement gas are different.

5. The measurement method as claimed in claim 1, wherein, for measuring a permeability of the hollow body to oxygen, the flushing gas is nitrogen and the measurement gas is nitrogen mixed with a proportion of hydrogen of between 0.5% and 5%.

6. The measurement method as claimed in claim 1, wherein the measuring of the quantity of the measurement gas is performed by coulometry.

7. An installation for implementing the method for measuring a permeability of a wall of a hollow body made from polymer material as described in claim 1, wherein the installation comprises a first circuit of a flushing gas suitable for flushing the hollow body and a second circuit of a measurement gas introduced into said hollow body, the first circuit and the second circuit being partly common and connected to one another via fluid distribution means so that the measurement gas is sent into said hollow body without mixing with said measurement gas.

8. The installation as claimed in claim 7, wherein the distribution means comprise at least two inlets and one outlet and wherein each inlet can be communicated selectively with the outlet.

9. The installation as claimed in claim 8, wherein:
    a first inlet of the distribution means is connected to a measurement gas distribution source associated with an instrument for measuring a quantity of a given gas;
    a second inlet of the distribution means is connected to a source of flushing gas;
    the outlet of the distribution means communicates fluidly with one side of said polymer wall; and
    said polymer wall side communicate communicates fluidly with the instrument for measuring the quantity of the given gas.

10. An application of the method as claimed in claim 1 or of the installation as claimed in claim 7 for measuring the permeability of a hollow body to oxygen or to carbon dioxide.

* * * * *